United States Patent [19]

Perkow et al.

[11] 4,044,045
[45] Aug. 23, 1977

[54] COMBATING PESTS WITH DI-(2-THIOUREIDO-(N-ALKOXYCARBONYL)-N-PHENYLUREIDO)-COMPOUNDS

[75] Inventors: Werner Perkow, Ahrensburg; Hans Hopp, Itzehoe; Walter Ingwersen, Nindorf, all of Germany

[73] Assignees: Norddeutsche Affinerie, Hamburg; C. F. Spiess & Sohn, Kleinkarlbach, both of Germany

[21] Appl. No.: 687,846

[22] Filed: May 19, 1976

[30] Foreign Application Priority Data

May 24, 1975 Germany ............................. 2523072

[51] Int. Cl.$^2$ ......................................... C07C 149/40
[52] U.S. Cl. .................................. 260/470; 424/300; 424/309; 71/98
[58] Field of Search ........................................ 260/470

[56] References Cited

U.S. PATENT DOCUMENTS

| 3,661,989 | 5/1972 | Nowakowski | 260/553 A |
| 3,734,961 | 5/1973 | Englehart | 260/553 A |

OTHER PUBLICATIONS

Weygard, Preparative Organic Chemistry, John Wiley & Sons, New York (1972) 410–411.

Primary Examiner—Howard T. Mars
Attorney, Agent, or Firm—Burgess, Dinklage & Sprung

[57] ABSTRACT

Di-[2-thioureido-(N-Alkoxycarbonyl)-N-phenylureides] of the formula

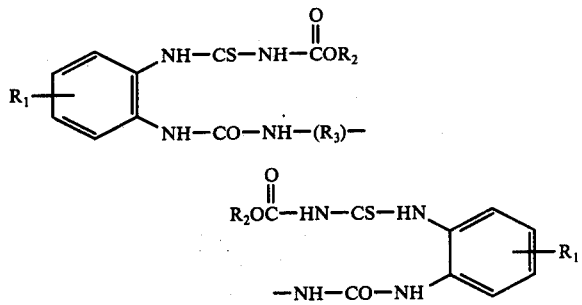

wherein
  $R_1$ is hydrogen, halogen, or an alkoxy or alkyl radical having 1 to 4 C atoms,
  $R_2$ is an alkyl radical having 1 to 4 C atoms, and
  $R_3$ is an alkylene radical having 3 to 10 C atoms, or a cycloalkylene or phenylene radical having 6 to 20 carbon atoms, are produced by reacting a 2-(3-alkoxycarbonyl-2-thioureido)-aniline of the formula

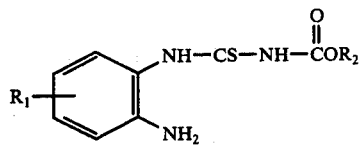

with a diisocyanate of the formula

ONC—(R$_3$)—CNO.

The compounds are active against fungi and other pests such as mites.

3 Claims, No Drawings

COMBATING PESTS WITH DI-(2-THIOUREIDO-(N-ALKOXYCARBONYL)-N-PHENYLUREIDO)-COMPOUNDS

This invention relates to novel diureide compounds having the structure

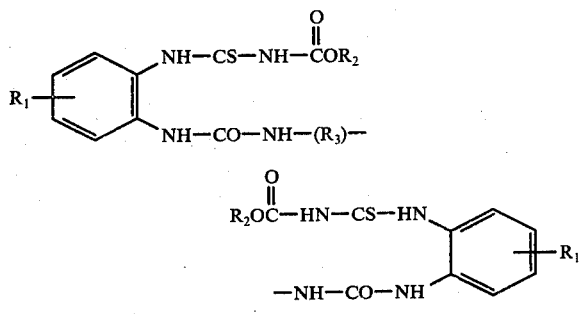

wherein
- $R_1$ is hydrogen, or an alkoxy or alkyl radical having 1 to 4 C atoms,
- $R_2$ is an alkyl radical having 1 to 4 C atoms, and
- $R_3$ is an alkylene radical having 3 to 10 C atoms, or a cycloalkylene or phenylene radical or a combination of an alkylene radical with cycloalkylene or phenylene radicals, the radicals having a total of 6 to 20 carbon atoms, and the production thereof and their use as a pesticide, particularly for controlling fungus diseases of cultivated plants. The compounds also exhibit activity against spider mites (*Tetranychus urticae*).

The novel compounds can be easily produced, have high chemical stability, desirable physical properties for being processed to provide a pesticide formulation, low mammalian toxicity and do not exert an irritating activity on the skin and mucous membranes. They have a systemic fungicidal activity because they are absorbed by the roots and foliage and are translocated to all parts of the plant. This apparently is responsible for protective as well as curative activities against a large number of fungus diseases which can cause considerable damage in agriculture. A particularly high activity, which is superior to that of other agents, is exerted against fungi of the Ascomycetes class of fungi. These include the fungi which cause

| | |
|---|---|
| mildew of cereals | (Erysiphe graminis) |
| mildew of apples | (Podosphera leucotricha) |
| mildew of cucumbers | (Erysiphe cichoacearum) |
| mildew of roses | (Sphaerotheca pannosa) |
| mildew of begonia | (Oidium begoniae) |
| scab disease in orchards | (Venturia inaequalis) |
| dry leaf and brown awn disease of wheat | (Septoria nodorum) |
| gray mold rot | (Botrytis cinerea). |

The novel compounds exhibit an excellent activity also against fungi of the Fusarium genus (particularly white mold, *Fusarium nivale*) and of the Phycomycetes class (particularly potato blight, *Phytophtohora infestans*) and Basidiomycetes class (particularly fungi causing rust and smut of cereals).

The novel compounds may be formulated in known manner with the aid of solvents, mineral or organic vehicles, wetting, dispersing, adhesive, emulsifying and other conventional adjuvant substances to form sprayable powders and dusts, concentrated emulsions, pastes, granules, sprayable aerosols, etc. The form in which they are prepared will depend on the specific application. They can be desirably combined with other pesticides, such as known fungicides or insecticides, herbicides, plant growth regulators, fertilizers, etc. The concentration of active material as applied may range from as low as a fraction of 1% almost up to 100%, depending upon the manner of application, as known.

The use of the novel compounds together with other fungicides, particularly of the class consisting of the dithiocarbamates (Mancozeb, Maneb, Propined) or halogen alkyl thioderivatives of tetrahydrophthalimide and phthalimide (Captan, Captafol, Folpet), or of organotin compounds (Fentinacetat), or wettable sulfur, has resulted in a surprising increase in actvity beyond the additive activity to be expected. The proportions by weight of the new to known fungicides may range from about 10:1 to 0.1:1, especially about 3:1 to 0.3:1.

Particularly suitable compounds are those having the structure

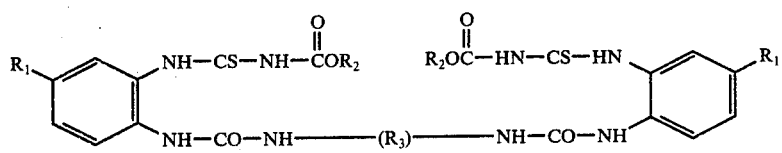

wherein $R_1$, $R_2$, and $R_3$ have the meanings defined hereinbefore.

The novel compounds are produced by reacting a 2-(3-alkoxycarbonyl-2-thioureido)-aniline, which is unsubstituted or additionally substituted at the phenyl ring, with a diisocyanate in accordance with the equation

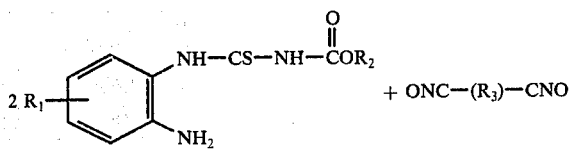

-continued

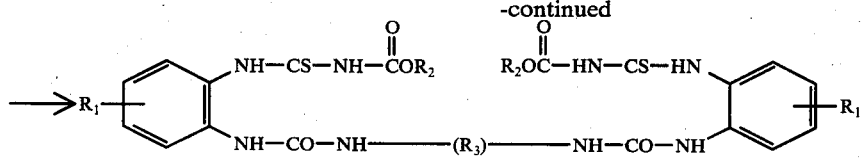

The reaction can be carried out at elevated temperature, e.g. about room temperature up to the boil, in an inert organic solvent, such as acetone or acetonitrile which contains the reactants in approximately stoichiometric quantities. Excesses of either reactant may be employed but are wasteful.

The production of the compounds according to the invention and the use thereof as fungicides will be explained more fully in the following examples wherein all parts are by weight unless otherwise expressed.

EXAMPLE 1

22.5 g finely powdered 2-(3-methoxycarbonyl-2-thioureido)-aniline (0.1 mole) and 10.5 g trimethyl-hexamethylene diisocyanate (0.05 mole) are heated in 100 ml acetone with stirring and refluxing. The reactants

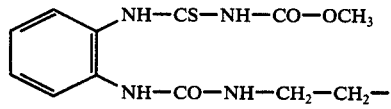

dissolve completely within about 1 hour, and the solid reaction product begins to separate shortly thereafter. When the heating has been continued for two additional hours, the reaction mixture is cooled and the precipitate is washed with acetone and ether and dried. The yield is 30–31 grams and the melting point is at 168°–171° C. The analytic composition corresponds to 1,6-di[2-thioureido-(N-methoxycarbonyl)-N-phenylureido]-trimethylhexane of the formula

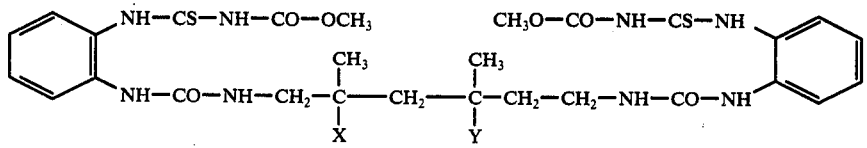

wherein one of X and Y is H and the other is —CH$_3$. Because the starting diisocyanate is available as a commercial product consisting of a mixture of approximately equal parts of 2,2,4-trimethyl-hexamethylene diisocyanate and 2,4,4-trimethyl-hexamethylene diisocyanate, the diureido compound is produced as a corresponding mixture of isomers.

EXAMPLE 2

When 2(3-alkoxy-carbonyl-2-thioureido)-aniline derivatives which are substituted at the R$_1$ and R$_2$ radicals in accordance with the following table are treated as described in Example 1, together with the same diisocyanate, the following reaction products are formed, which are defined by their stated melting points:

|    | R$_1$    | R$_2$   | Melting point, ° C |
|----|----------|---------|--------------------|
| a) | 4-OCH$_3$ | CH$_3$  | 178 with decomp.   |
| b) | 4-OC$_2$H$_5$ | CH$_3$ | 174 with decomp.   |
| c) | 4-OCH$_3$ | C$_2$H$_5$ | 176 with decomp. |
| d) | 4-Cl     | C$_2$H$_5$ | above 220        |
| e) | 4-CH$_3$ | CH$_3$  | above 220          |

EXAMPLE 3

When 1 mole of hexamethylene diisocyanate and 2 moles of 2-(3-methoxycarbonyl-2-thioureido)-aniline are treated as described in Example 1, a compound is formed which has the structure

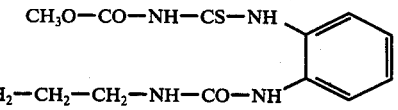

and a melting point of 165° C.

EXAMPLE 4

When 1 mole of isophorone diisocyanate and 2 moles of 2-(3-alkoxycarbonyl-2-thioureido)-aniline are treated as described in Example 1, compounds are formed which have the structure

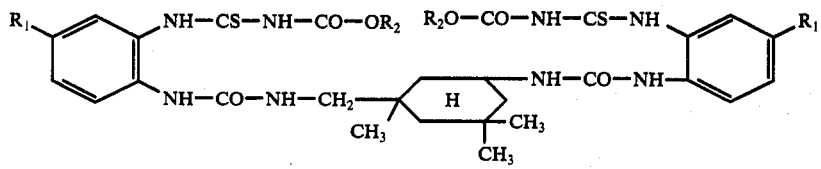

The novel compounds are obtained in a yield above 90% and are defined by the melting points stated in the following table:

|    | R$_1$      | R$_2$      | Melting point, ° C   |
|----|------------|------------|----------------------|
| a) | H          | CH$_3$     | above 225            |
| b) | —OCH$_3$   | C$_2$H$_5$ | 174 with decomp.     |
| c) | OCH$_3$    | CH$_3$     | 171 with decomp.     |
| d) | OC$_2$H$_5$ | CH$_3$    | 213 with decomp.     |
| e) | Cl         | C$_2$H$_5$ | 228–230 with decomp. |
| f) | CH$_3$     | CH$_3$     | above 225            |

EXAMPLE 5

When 1 mole of 2,2-bis(4-isocyanatocyclohexyl)-propane and 2 moles of 2-(3-methoxycarbonyl-2-thioureido)-aniline are treated as described in Example 1, a compound is formed which has the structure

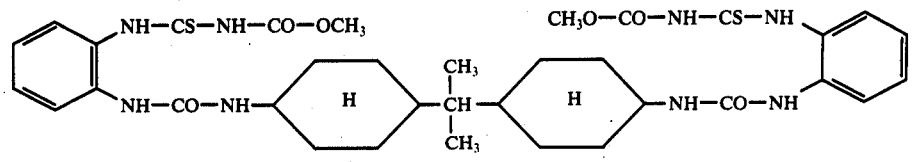

and a melting point of 181° C.

EXAMPLE 6

When 1 mole of bis(4-isocyanatocylohexyl)-methane and 2 moles of 2-(3-ethoxycarbonyl-2-thioureido)-aniline are treated as described in Example 1, a compound is formed which has the structure

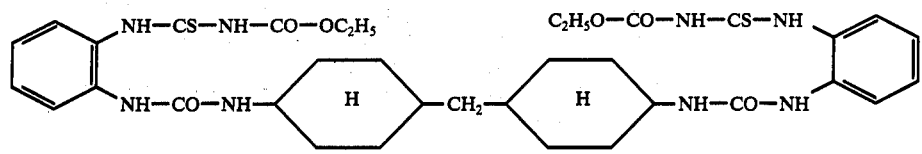

and a melting point of 189° C.

EXAMPLE 7

When 1 mole of bis-(3-methyl-4-isocyanatocyclohexyl)-methane and 2 moles of 2-(3-methoxycarbonyl-2-thioureido)-aniline are treated as described in Example 1, a compound is formed which has the structure

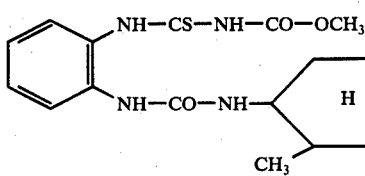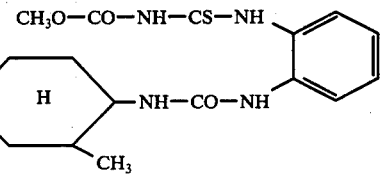

and a melting point of 163° C.

EXAMPLE 8

When 1 mole of diphenylmethane-4,4-diisocyanate and 2 moles 2-(3-methoxycarbonyl-2-thioureido)-aniline are treated as described in Example 1, a compound is formed which has the structure

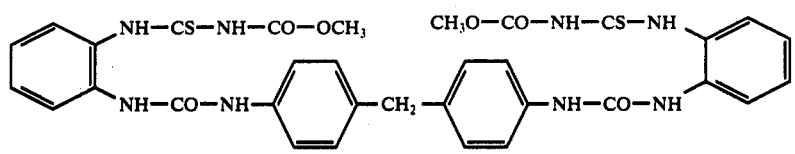

and a melting point of 183° C.

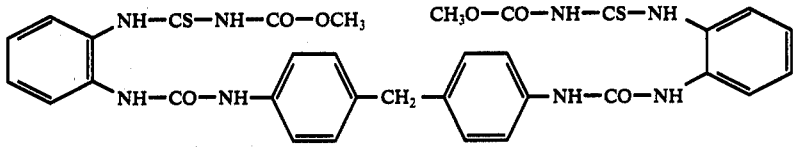

and a melting point of 183° C.

EXAMPLE 9

When 1 mole of toluylene-2,4-diisocyanate and 2 moles of 2-(3-ethoxycarbonyl-2-thioureido)-aniline are treated as described in Example 1, a compound is formed which has the structure

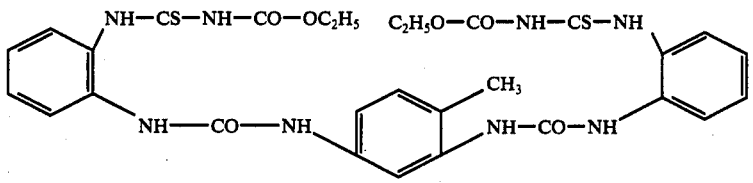

and a melting point of 181° C.

EXAMPLE 10

50% of the compound produced in Example 4 and 50% talc or chalk were homogeneously ground and blended to produce a powder which is eminently suitable for treating cereal seeds. Winter wheat seeds infected with Septoria nodorum were treated with the quantities stated in the following table. 5 portions of 100 grains each were then placed in bowls which contained sterilized soil, and were held therein at 15° C for 3 weeks. The percentage of the plants which had germinated and the condition thereof were recorded.

| Quantity of pesticide used in grams per 100 kg of seeds | % Germination | Percentage of germinated plants which were healthy |
| --- | --- | --- |
| 100 | 75 | 74 |
| 200 | 85 | 82 |
| 300 | 93 | 89 |
| 400 | 95 | 93 |
| untreated | 20 | 0 |

EXAMPLE 11

In the manner described in Example 10, a seed-treating material was prepared which contained 50% of an active substance consisting of the compound produced in accordance with Example 1. Winter wheat seeds which had been artificially infected with spores of *Ustilage tritici*, which causes loose smut of wheat, were placed in October into Mitscherlich vessels and held in a greenhouse at 10° C. The plants were brought into the open in December, in the trifoliate stage, and were left there until the ears were ripe. The number of healthy ear-carrying plants is given in the following table:

| Quantity of seed-treating material in grams per 100 kg of seeds | Percentage of plants which were healthy when the ears were ripe |
| --- | --- |
| 50 | 50 |
| 100 | 99 |
| 150 | 100 |
| — | 2 |

EXAMPLE 12

A concentrate which can be emulsified in water was prepared from 30% by weight of the compound produced in accordance with Example 2a, 40% N-methyl-pyrrolidone, and 30% of a non-ionic emulsifying agent of the nonylphenolpolyglycol ether type. Wheat plants in the bifoliate stage were sprayed with an aqueous emulsion having the concentration stated in the table and in the trifoliate stage were artificially infected with yellow rust (*Puccinia glumarum*) and rated for their state 5 weeks after the infection. The damage was determined by the quantity of withered leaf portions related to the healthy leaf material.

| Percentage of active material in sprayed liquor | Percentage of withered leaf material |
| --- | --- |
| 0.05 | 35 |
| 0.10 | 20 |
| 0.15 | 7 |
| 0.20 | 3 |
| 0.25 | 1 |
| 0.30 | 0 |
| 0.00 | 75 |

EXAMPLE 13

A concentrate which can be emulsified in water was prepared from 25% of the compound produced in accordance with Example 8, 15% N-methyl pyrrolidone, 25% alpha-methyl naphthalene, and 35% of a non-ionic emulsifying agent of the nonylphenolpolyglycol ether type.

Red Polyantha roses which had been artificially infected with mildew (*Sphaerotheca pannosa*) were sprayed dripping wet with an aqueous liquor which contained 0.15% of the above-mentioned concentrate at the time of the first occurrence of light-colored coverings due to an infection. The growth of the fungi was inhibited almost at once and the protection afforded by the agent persisted for several weeks. Undesired spots which were due to the spray did not occur. As an additional pesticidal activity, a distinct secondary action on spider mites (*Tetranychus urticae*) has been observed, i.e. the compounds are active against arthropods, particularly acarids, and especially mites.

It will be appreciated that the instant specification and examples are set forth by way of illustration and not limitation, and that various modifications and changes may be made without departing from the spirit and scope of the present invention.

What is claimed is:

1. Di-[2-thioureido-(N-alkoxycarbonyl)-N-phenylureides] of the formula

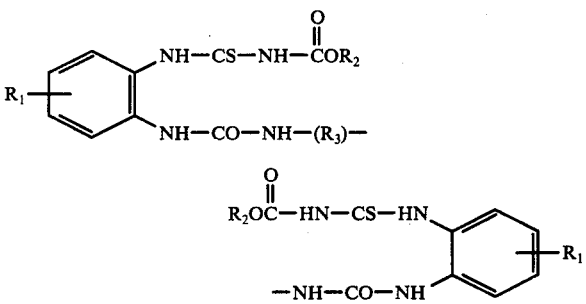

wherein
R₁ is hydrogen, halogen, or an alkoxy or alkyl radical having 1 to 4 C atoms,
R₂ is an alkyl radical having 1 to 4 C atoms, and
R₃ is an alkylene radical having 3 to 10 C atoms, or a cycloalkylene or phenylene radical, or a combination of an alkylene radical with cycloalkylene or phenylene radicals, the radicals having a total of 6 to 20 carbon atoms.

2. A compound according to claim 1 having the structure

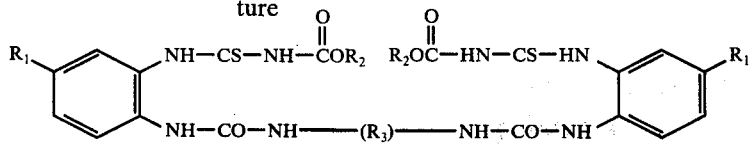

3. A compound according to claim 1, in which R₃ is a cyclohexylene radical or a combination of an alkylene radical with a cyclohexylene radical.

* * * * *